United States Patent [19]

Klein

[11] 4,220,665
[45] Sep. 2, 1980

[54] BACTERIOSTATIC COMPOSITION AND METHOD

[75] Inventor: Erich Klein, Holzminden, Fed. Rep. of Germany

[73] Assignee: Dragoco Gerberding & Co GmbH, Holzminder, Fed. Rep. of Germany

[21] Appl. No.: 914,723

[22] Filed: Jun. 12, 1978

[30] Foreign Application Priority Data

Jun. 27, 1977 [DE] Fed. Rep. of Germany ....... 2728921

[51] Int. Cl.³ .................... A01N 31/00; A61K 31/045
[52] U.S. Cl. ................................ 424/343; 252/522R; 424/65
[58] Field of Search ................................ 424/343, 65

[56] References Cited

U.S. PATENT DOCUMENTS 4,070,449  1/1978  Rowsell et al. .................... 424/65 X

OTHER PUBLICATIONS

Hackh's Chemical Dictionary—4th ed., 1969, p. 261.
Merck Index—9th ed., 1976, p. 516 (3878).

*Primary Examiner*—Leonard Schenkman
*Attorney, Agent, or Firm*—Browdy and Neimark

[57] ABSTRACT

The invention concerns a bacteriostatic composition and method employing 3,7,11-trimethyl-dodeca-2,6,10-trien-1-ol as bacteriostactically active agent.

5 Claims, No Drawings

BACTERIOSTATIC COMPOSITION AND METHOD

The present invention relates to a bacteriostatic composition and method of combating growth of certain Gram-positive skin bacteria.

A large number of various bacteria settle on the human skin. These are mostly non-pathogenic and do not affect skin condition or odor. Others, by their presence, on the other hand, prevent penetration of pathogenic bacteria which cause disease of portions of the skin. The degeneration of normally substantially odorless or weakly smelling substances contained in perspiration by the bacterial flora of the skin, leads to formation of products having an unpleasant odor which can be of considerable discomfort to the person affected.

For the purpose of removing such products having an unpleasant odor, or for the purpose of preventing their formation, cosmetic preparations are employed which either reduce perspiration at the skin surface (antiperspirant) or which substantially destroy the natural bacterial flora of the skin (bacteriocidal deodorants). In both cases significant disruptions of natural conditions at the skin surface occur. The deodorants which are of particular interest here practically always comprise strongly halogenated phenol compounds, the use of which is according to most recent knowledge not necessarily without problem, and in view of their strong bacteriocidal activity destroy practically all bacterial skin flora.

Products are therefore being sought which prevent or strongly diminish growth of bacterial flora of the skin, which are present also after conventional bathing, which products however do not further disturb the natural equilibrium of biological procedures at the surface of the skin.

It has now been found that the substance farnesol (3,7,11-trimethyl-dodeca-2,6,10-trien-1-ol) which occurs widely in nature, is higly effective in inhibiting the growth of odor-forming bacterial flora of the skin at relatively low concentrations, without influencing the biological equilibrium at the skin surface.

The invention accordingly relates to the use of farnesol as a bacteriostatic agent, or a component thereof, in cosmetic products for application to the human skin.

Although farnesol has long been known to be present in ether oils, and experimentation has been carried out on the bacteriostatic or bacteriocidal activity of such ether oils, the bacteriostatic activity of the natural substance farnesol has remained unrecognized. This is no doubt to be attributed to the fact that farnesol is normally present in the ether oils in extremely low amounts and that the concentration, at which a bacteriostatic activity is exhibited, has not been reached.

It has been found that at a concentration of more than 0.15% by weight of farnesol, calculated on the total weight of the composition or cosmetic product, a significant bacteriostatic activity is exhibited. At a concentration of 0.3% by weight of farnesol, a complete inhibition of the odor-forming Gram-positive bacteria *Staphylococcus aureus* and *Staphylococcus epidermidis* as well as an effective inhibition of Coryne-bacterium spec. takes place. Here, the sensitivity to farnesol of the pathogenic Staphylococcus (*Staph. aureus*) is greater than the epidermal Staphylococcus (*Staph. epidermidis*). The growth of pathogenic Staphylococcus is completely inhibited at a concentration of 0.2% farnesol. Growth of gram-negative bacteria and yeasts is not inhibited by farnesol. A definite fall in activity of farnesol is observed at a concentration of 0.15% so that this is the lower concentration limit for useful products, at least for products to be employed for achieving incomplete inhibition.

For cosmetic preparations, a farnesol concentration of 0.25% is sufficient in all circumstances. The minimum inhibition concentration to achieve a total inhibition of growth of the odor-forming Gram-positive bacteria to be observed is 0.3%, whereby it is however to be noted that a total inhibition is not in all circumstances desirable. All percentage contents which are here given are percentum by weight.

Important for the usefulness of farnesol as a bacteriostatic in the cosmetic field is the duration of action in practical application, the so-called depot effect. This activity was tested with the aid of a "contact growth index method", in which pieces of filter paper are treated with 0.2 ml of an alcoholic solution of corresponding concentration, dried and then exposed for different time periods to a medium having a 90% relative humidity at 37° C. These pre-treated samples were then tested for their contact growth index with *Staphylococcus aureus* and *Staphylococcus epidermidis* as well as Corynebacterium spec. These tests show that a cosmetically significant depot effect is definitely present for a period of 6 hours, which is in practice adequate for deodorant remanence.

Since farnesol can also be employed as a component of perfume compositions, such compositions having a correspondingly high content of farnesol were tested for their bacteriostatic activity. The activity of such farnesol-rich perfume compositions could similarly be clearly shown. Antagonistic effects due to the presence of other components of the perfume composition could not be determined. Since the amount of perfume in cosmetic finished products is normally from about 0.5 to about 1%, a perfume or perfume oil which comprises farnesol as active bacteriostatic must consist of from about 30 to about 60% farnesol. Farnesol as a sesquiterpene alcohol possesses only a relatively weak smell, but has good fixative properties and can thus be employed without reservation in high concentrations as a component of perfume compositions.

The following Tables provide a survey of the microbiological test results obtained with farnesol as substance and with perfume compositions containing farnesol. The same perfume compositions, without farnesol, show practically no inhibition in the test.

Table 1

Results of the contact growth index test of farnesol as against different types of micro-organisms at different concentrations.

| Formulation | Concentration | Application | Contact Growth Index Against | | | | | | |
|---|---|---|---|---|---|---|---|---|---|
| | | | Staph. aureus SG 511 | Staph. epid. | Coryne-bact. spec. | E. colli | Aerob. Klebs. | Pseud. pyoc. | Candi albio |
| Farnesol | 0.3% | 0.2 ml/15.9 cm² | 0 | 0 | 1 | 4 | 4 | 4 | 4 |
| " | 0.25% | " | 0 | 1 | 1-2 | 4 | 4 | 4 | 4 |

Table 1-continued

Results of the contact growth index test of farnesol as against different types of micro-organisms at different concentrations.

| Formulation | Concentration | Application | Staph. aureus SG 511 | Staph. epid. | Corynebact. spec. | E. colli | Aerob. Klebs. | Pseud. pyoc. | Candi albio |
|---|---|---|---|---|---|---|---|---|---|
| " | 0.2% | " | 0 | 1–2 | 2–3 | 4 | 4 | 4 | 4 |
| " | 0.15% | " | 3 | 3–4 | 4 | 4 | 4 | 4 | 4 |
| " | 0.1% | " | 3–4 | 4 | 4 | 4 | 4 | 4 | 4 |
| 96% Ethyl-alcohol | conc. | " | 4 | 4 | 4 | 4 | 4 | 4 | 4 |

Table 2

Results of the contact growth index test at o.3% concentration of farnesol after physical treatment by temperature and increased humidity after different times.

| Formulation | Application | Bacteria type | 1 | 2 | 4 | 6 | 12 | 24 hours |
|---|---|---|---|---|---|---|---|---|
| Farnesol o.3% | 0.2 ml/15.9 cm² | Staph. aureus SG 511 | 0 | 0 | 0 | 0–1 | 4 | 4 |
| " | " | Staph. epiderm. | 0 | 0 | 0 | 0–1 | 4 | 4 |
| " | " | Corynebact. spec. | 0 | 0 | 0 | 2–3 | 4 | 4 |
| 96% Ethyl-alcohol | " | Staph. aureus SG 511 Staph. epid. Corynebact. spec. | 4 | 4 | 4 | 4 | 4 | 4 |

Contact growth index of coated plates left at 37° C. and 90% relative humidity after

Table 3

Results of the contact growth index test of different formulations in 0.6% alcohol solution against *Staphylococcus epidermidis* and *Corynebacterium spec.* Perfume oils were mixed at a 1:1 ratio with farnesol and tested in parallel with the perfume without farnesol.

| Perfume oil | Concentration | Application | Staphyloc. epidermidis | Corynebact. |
|---|---|---|---|---|
| DR 9195-1/50% Farnesol | 0.6% | 0.2 ml/ 15.9 cm² | 0 | 0 |
| DR 0/9230/50% Farnesol | 0.6% | 0.2 ml/ 15.9 cm² | 0 | 1 |
| DR 0/9195/50% Farnesol | 0.6% | 0.2 ml/ 15.9 cm² | | |
| DR 0/9279/50% Farnesol | 0.6% | 0.2 ml/ 15.9 cm² | 0 | 0 |
| DR 9195-1 | 0.6% | 0.2 ml/ 15.9 cm² | 3–4 | 4 |
| DR 0/9230 | 0.6% | 0.2 ml/ 15.9 cm² | 4 | 4 |
| DR 0/9195 | 0.6% | 0.2 ml/ 15.9 cm² | 4 | 4 |
| DR 0/9279 | 0.6% | 0.2 ml/ 15.9 cm² | 4 | 4 |
| Deodorant Spray Lavender | 0.6% | 0.2 ml/ 15.9 cm² | 4 | 4 |
| Ethyl alcohol | 96.0% | 0.2 ml/ 15.9 cm² | 4 | 4 |

Note: The above numbers are employed to identify perfume oils the base composition of which is shown on pages 10 to 13.

It can be seen from above that a content of at least 0.15% by weight of farnesol in cosmetic products leads to a good bacteriostatic activity on Gram-positive epidermal bacterial flora. A content of at least 0.2% leads to a complete inhibition of the growth of pathogenic Staphylococcus and is sufficient for many purposes, for example for deodorants where a content of 0.2 to 0.5% farnesol is suitable.

Where demands are greater, the lower concentration limit is 0.25% farnesol and for cosmetic products with which a substantially complete or complete inhibition of growth of Gram-positive bacteria should be obtained, farnesol should be present at a concentration of 0.3% or more. For practical reasons, at most 1% farnesol would be included in cosmetic products, although basically there is no upper limit.

| DR 9195-1 | |
|---|---|
| 60 g | Phenyl Ethyl Alcohol |
| 50 g | Bencyl Acetate |
| 350 g | Hexyl Cinnamic Aldehyde alpha |
| 280 g | Hydroxy citronellal |
| 120 g | Bergamott Oil |
| 50 g | Lemon Oil |
| 30 g | Citronellol |
| 40 g | Lavandin Oil |
| 40 g | Styrallyl Acetate |
| 20 g | Lyral |
| 40 g | Galaxolide |
| 20 g | Linalyl Acetate |
| 20 g | Linalool |
| 20 g | Rhodinol |
| 20 g | Phenyl ethyl dimethyl carbinol |
| 20 g | Bencyl Salicylate |
| 20 g | Nerolidol |
| 1200 g | |

| DR 9230 | |
|---|---|
| 100 g | Litsea Cubeba Oil |
| 140 g | Bergamott Oil |
| 40 g | Galbanum Oil |
| 140 g | Lemon Oil |
| 60 g | Methyl Ionone |
| 120 g | Vetikone |
| 40 g | Ylang Ylang Oil |
| 40 g | Coumarin |
| 50 g | Phenyl Ethyl Alcohol |
| 20 g | Styralyl Acetate |
| 40 g | Sauge Sclaree |
| 10 g | Storax Resinoid |
| 40 g | Peppermint Oil |
| 40 g | Menthanyl Acetate |
| 10 g | Aldehyde C 12 MNA |
| 60 g | Dimyrcetol |
| 10 g | Macis Oil |
| 40 g | Citronellyl Nitrile |
| 1000 g | |

| DR 9195 | |
|---|---|
| 160 g | Hydroxy citronellal |
| 120 g | Phenyl Ethyl Alcohol |
| 200 g | Hexyl Cinnamic Aldehyde alpha |
| 100 g | Bencyl Acetate |
| 40 g | Ylang Ylang Oil |
| 40 g | Lyral |
| 50 g | Lilial |
| 60 g | Patchouly Oil |
| 80 g | Galaxolide |
| 40 g | Isoeugenol |
| 40 g | Labdanum Extract |
| 20 g | Coumarin |
| 40 g | Linalool |
| 10 g | Isobutyl chinoline |
| 1000 g | |

| DR 9279 | |
|---|---|
| 200 g | Diheptyl Acetate |
| 80 g | Bencyl Acetate |
| 90 g | Amyl Cinnamic Aldehyde alpha |
| 90 g | Lilial |
| 30 g | Amyl Salicylate |
| 60 g | Hydroxycitronellal |
| 30 g | Ylang Ylang Oil |
| 60 g | Cedren Epoxide |
| 20 g | Coumarin |
| 50 g | Terpineol |
| 90 g | Bergamott Oil |
| 50 g | Petitgrain Oil |
| 50 g | Eucalyptus Oil |
| 80 g | Orange Oil |
| 40 g | Dimyrcetol |
| 180 g | Phenyl Ethyl Alcohol |
| 1200 g | |

What is claimed is:

1. A method of combatting growth of Gram-positive skin bacterial flora, comprising the step of applying to Gram-positive bacteria on a skin surface a bacteriostatically effective amount of 3,7,11-trimethyl-dodeca-2,6,10-trien-1-ol.

2. A method according to claim 1, in which the 3,7,11-trimethyl-dodeca-2,6,10-trien-1-ol is comprised in a cosmetic formulation, the concentration of the 3,7,11-trimethyl-dodeca-2,6,10-trien-1-ol in the formulation being at least 0.15% by weight.

3. A method according to claim 2, in which the concentration of the 3,7,11-trimethyl-dodeca-2,6,10-trien-1-ol in the formulation is from 0.2 to 1% by weight.

4. A method according to claim 2, in which the formulation is a perfume formulation.

5. A method according to claim 2, wherein said Gram-positive skin bacterial flora comprise *Staphylococcus aureus* and *Staphylococcus epidermidis*.